(12) United States Patent
Thomson

(10) Patent No.: US 7,005,252 B1
(45) Date of Patent: Feb. 28, 2006

(54) SERUM FREE CULTIVATION OF PRIMATE EMBRYONIC STEM CELLS

(75) Inventor: James A Thomson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/522,030

(22) Filed: Mar. 9, 2000

(51) Int. Cl.
- *A01N 1/00* (2006.01)
- *C12Q 1/00* (2006.01)
- *C12P 1/00* (2006.01)
- *C12N 5/00* (2006.01)
- *C12N 5/06* (2006.01)

(52) U.S. Cl. .................. 435/1.1; 435/325; 435/326; 435/4; 435/41; 800/8

(58) Field of Classification Search ................ 435/325, 435/326, 1.1, 405, 70.1, 283.1; 424/93.1; 800/8
See application file for complete search history.

(56) References Cited

U.S. PATENT DOCUMENTS

| | | | |
|---|---|---|---|
| 5,405,772 A | 4/1995 | Ponting | |
| 5,453,357 A | 9/1995 | Hogan | |
| 5,670,372 A | 9/1997 | Hogan | |
| 5,690,926 A | 11/1997 | Hogan | |
| 5,843,780 A | 12/1998 | Thomson | |
| 6,200,806 B1 * | 3/2001 | Thomson | 435/366 |
| 6,245,566 B1 * | 6/2001 | Gearhart et al. | 435/384 |
| 2002/0081724 A1 | 6/2002 | Carpenter et al. | |

FOREIGN PATENT DOCUMENTS

| | | |
|---|---|---|
| DE | 19756864 C1 | 12/1997 |
| WO | 97/47734 | 12/1997 |
| WO | 98/30679 | 7/1998 |
| WO | 99/20741 | 4/1999 |
| WO | 00/68359 | 11/2000 |

OTHER PUBLICATIONS

JA Thomson et al., Proc.Natl.Acad.Sci USA, "Isolation of a primate embryonic stem cell line," Aug. 1995, vol. 92, pp. 7844-7848.*

MD Goldsborough et al., Focus, "Serum-Free Culture of Murine Embryonic Stem (ES) Cells,"1998, vol. 20, No. 1,pp. 8-12.*

AJ Clark et al., Transgenic Animals, "Germ line manipulation: applications in agriculture and biotechnology," Chap. 11, p. 250.*

J Nichols et al., Development,"Establishment of germ-line-competent embryonic stem (ES) cells using differentiation inhibiting activity," 1990, 110, pp. 1341-1348.*

JA Piedrahita et al., Theriogenology," On the Isolation of Embryonic Stem Cells: Comparative Behavior of Murine, Procine and Ovine Embryos," Nov. 1990, vol. 34, No. 5, pp. 879-901.*

YP Cruz et al., Animal Applications of Research in Mammalian Deveolpment,"Origin of Embryonic and Extraembryonic Cell Lineages in Mammalian Embryos," pp. 147-204.*

J. Thomson et al., Embryonic Stem Cell Llnes Drived From Human Blastocysts, 282 Science 1145-1147 (1998).

J. Rossant et al., In Search Of The tabula rasa Of Human Cells, 17 Nature Biotechnology 23-4 (1999).

J. Gearhart, New Potential For Human Embryonic Stem Cells, 282 Science 1061-2 (1998).

T. Yamaguchi et al., Expression Of The Fibroblast Growth Factor Receptor FGFR-1/flg During Gastrulation And Segmentation In the Mouse Embryo, 152 Dev. Biol. 75-88 (1992).

Mummery et al., "Fibroblast Growth Factor-Mediated Growth Regulation and Receptor Expression in Embryonal Carcinoma and Embryonic Stem Cells and Human Germ Cell Tumours," *Biochemical and Biophysical Research Communications* 191:188-195 (1993).

Pease et al., "Isolation of Embryonic Stem (ES) Cells in Media Supplemented with Recombinant Leukemia Inhibitory Factor (LIF)," *Developmental Biology* 141:344-352 (1990).

* cited by examiner

*Primary Examiner*—Joseph Woitach
(74) *Attorney, Agent, or Firm*—Quarles & Brady, LLP

(57) ABSTRACT

Disclosed herein are methods for culturing primate embryonic stem cells. These cells are cultured on a prolonged and stable basis in the presence of exogenously supplied fibroblast growth factor and in the absence of animal serum. Preferably there is also a fibroblast feeder layer. Also disclosed is a culture media containing fibroblast feeder layer and the fibroblast growth factor.

14 Claims, No Drawings

SERUM FREE CULTIVATION OF PRIMATE EMBRYONIC STEM CELLS

CROSS REFERENCES TO RELATED APPLICATIONS

Not applicable.

STATEMENT REGARDING FEDERALLY SPONSORED RESEARCH

BACKGROUND OF THE INVENTION

The present invention relates to methods for culturing primate embryonic stem cell cultures and culture media useful therewith.

Primate (e.g. monkey and human) pluripotent embryonic stem cells have been derived from preimplantation embryos. See U.S. Pat. No. 5,843,780 and J. Thomson et al., 282 Science 1145–1147 (1998). The disclosure of these publications and of all other publications referred to herein are incorporated by reference as if fully set forth herein. Notwithstanding prolonged culture, these cells stably maintain a developmental potential to form advanced derivatives of all three embryonic germ layers.

Primate (particularly human) ES cell lines have widespread utility in connection with human developmental biology, drug discovery, drug testing, and transplantation medicine. For example, current knowledge of the postimplantation human embryo is largely based on a limited number of static histological sections. Because of ethical considerations the underlying mechanisms that control the developmental decisions of the early human embryo remain essentially unexplored.

Although the mouse is the mainstay of experimental mammalian developmental biology, and although many of the fundamental mechanisms that control development are conserved between mice and humans, there are significant differences between early mouse and human development. Primate/human ES cells should therefore provide important new insights into their differentiation and function.

Differentiated derivatives of primate ES cells could be used to identify gene targets for new drugs, used to test toxicity or teratogenicy of new compounds, and used for transplantation to replace cell populations in disease. Potential conditions that might be treated by the transplantation of ES cell-derived cells include Parkinson's disease, cardiac infarcts, juvenile-onset diabetes mellitus, and leukemia. See e.g. J. Rossant et al. 17 Nature Biotechnology 23–4 (1999) and J. Gearhart, 282 Science 1061–2 (1998).

Long term proliferative capacity, developmental potential after prolonged culture, and karyotypic stability are key features with respect to the utility of primate embryonic stem cell cultures. Cultures of such cells (especially on fibroblast feeder layers) have typically been supplemented with animal serum (especially fetal bovine serum) to permit the desired proliferation during such culturing.

For example, in U.S. Pat. Nos. 5,453,357, 5,670,372 and 5,690,296 various culture conditions were described, including some using a type of basic fibroblast growth factor together with animal serum. Unfortunately, serum tends to have variable properties from batch to batch, thus affecting culture characteristics.

In WO 98/30679 there was a discussion of providing a serum-free supplement in replacement for animal serum to support the growth of certain embryonic stem cells in culture. The serum replacement included albumins or albumin substitutes, one or more amino acids, one or more vitamins, one or more transferrins or transferrin substitutes, one or more antioxidants, one or more insulins or insulin substitutes, one or more collagen precursors, and one or more trace elements. It was noted that this replacement could be further supplemented with leukemia inhibitory factor, steel factor, or ciliary neurotrophic factor. Unfortunately, in the context of primate embryonic stem cell cultures (especially those grown on fibroblast feeder layers), these culture media did not prove satisfactory.

In the context of nutrient serum culture media (e.g. fetal bovine serum), WO 99/20741 discusses the benefit of use of various growth factors such as bFGF in culturing primate stem cells. However, culture media without nutrient serum is not described.

In U.S. Pat. No. 5,405,772 growth medium for hematopoietic cells and bone marrow stromal cells are described. There is a suggestion to use fibroblast growth factor in a serum-deprived media for this purpose. However, conditions for growth primate of embryonic stem cells are not described.

It can therefore be seen that a need still exists for techniques to stably culture primate embryonic stem cells without the requirement for use of animal serum.

BRIEF SUMMARY OF THE INVENTION

In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form the culture also has a fibroblast feeder layer.

Fibroblast growth factors are essential molecules for mammalian development. There are currently nine known fibroblast growth factor ligands and four signaling fibroblast growth factor receptors therefor (and their spliced variants). See generally D. Ornitz et al., 25 J. Biol. Chem. 15292–7 (1996); U.S. Pat. No. 5,453,357. Slight variations in these factors are expected to exist between species, and thus the term fibroblast growth factor is not species limited. However, I prefer to use human fibroblast growth factors, more preferably human basic fibroblast growth factor produced from a recombinant gene. This compound is readily available in quantity from Gibco BRL-Life Technologies and others.

It should be noted that for purposes of this patent the culture may still be essentially free of the specified serum even though a discrete component (e.g. bovine serum albumin) has been isolated from serum and then is exogenously supplied. The point is that when serum itself is added the variability concerns arise. However, when one or more well defined purified component(s) of such serum is added, they do not.

Preferably the primate embryonic stem cells that are cultured using this method are human embryonic stem cells that are true ES cell lines in that they: (i) are capable of indefinite proliferation in vitro in an undifferentiated state; (ii) are capable of differentiation to derivatives of all three embryonic germ layers (endoderm, mesoderm, and ectoderm) even after prolonged culture; and (iii) maintain a normal karyotype throughout prolonged culture. They are therefore referred to as being pluripotent.

The culturing permits the embryonic stem cells to stably proliferate in culture for over one month (preferably over six months; even more preferably over twelve months) while maintaining the potential of the stem cells to differentiate into derivatives of endoderm, mesoderm, and ectoderm tissues, and while maintaining the karyotype of the stem cells.

In another aspect the invention provides another method of culturing primate embryonic stem cells. One cultures the stem cells in a culture essentially free of mammalian fetal serum (preferably also essentially free of any animal serum) and in the presence of a growth factor capable of activating a fibroblast growth factor signaling receptor, wherein the growth factor is supplied from a source other than just a fibroblast feeder layer. While the growth factor is preferably a fibroblast growth factor, it might also be other materials such as certain synthetic small peptides (e.g. produced by recombinant DNA variants or mutants) designed to activate fibroblast growth factor receptors. See generally T. Yamaguchi et al., 152 Dev. Biol. 75–88 (1992)(signaling receptors).

In yet another aspect the invention provides a culture system for culturing primate embryonic stem cells. It has a fibroblast feeder layer and human basic fibroblast growth factor supplied by other than just the fibroblast feeder layer. The culture system is essentially free of animal serum.

Yet another aspect of the invention provides cell lines (preferably cloned cell lines) derived using the above method. "Derived" is used in its broadest sense to cover directly or indirectly derived lines.

Variability in results due to differences in batches of animal serum is thereby avoided. Further, it has been discovered that avoiding use of animal serum while using fibroblast growth factor can increase the efficiency of cloning.

It is therefore an advantage of the present invention to provide culture conditions for primate embryonic stem cell lines where the conditions are less variable and permit more efficient cloning. Other advantages of the present invention will become apparent after study of the specification and claims.

DETAILED DESCRIPTION OF THE PREFERRED EMBODIMENTS

In the following experiments I used the methods and culture systems of the invention to culture human ES cell lines. Two clonally derived human ES cell lines proliferated for over eight months after clonal derivation and maintained the ability to differentiate to advanced derivatives of all three embryonic germ layers.

Techniques for the initial derivation, culture, and characterization of the human ES cell line H9 were described in J. Thomson et al., 282 Science 1145–1147 (1998). In my experiments herein human ES cells were then plated on irradiated (35 gray gamma irradiation) mouse embryonic fibroblast. Culture medium for the present work consisted of 80% "KnockOut"™ Dulbeco's modified Eagle's medium (DMEM) (Gibco BRL, Rockville, Md.), 1 mM L-Glutamine, 0.1 mM-mercaptoethanol, and 1% nonessential amino acids stock (Gibco BRL, Rockville, Md.), supplemented with either 20% fetal bovine serum (HyClone, Logan, Utah) or 20% KnockOut™ SR medium adjuvant, a serum-free replacement originally optimized for mouse ES cells (Gibco BRL, Rockville, Md.). The components of KnockOut™ SR medium adjuvant are those described for serum replacements in WO 98/30679.

In alternative experiments medium was supplemented with either serum or the aforesaid serum replacer KnockOut™ SR medium adjuvant, and either with or without human recombinant basic fibroblast growth factor (bFGF, 4 ng/ml). The preferred concentration range of bFGF in the culture is between 0.1 ng/ml to 500 ng/ml.

To determine cloning efficiency under varying culture conditions, H-9 cultures were dissociated to single cells for 7 minutes with 0.05% trypsin/0.25% EDTA, washed by centrifugation, and plated on mitotically inactivated mouse embryonic fibroblasts ($10^5$ ES cells per well of a 6-well plate). To confirm growth from single cells for the derivation of clonal ES cell lines, individual cells were selected by direct observation under a stereomicroscope and transferred by micropipette to individual wells of a 96 well plate containing mouse embryonic fibroblasts feeders with medium containing 20% serum replacer and 4 ng/ml bFGF.

Clones were expanded by routine passage every 5–7 days with 1 mg/ml collagenase type IV (Gibco BRL, Rockville, Md.). Six months after derivation, H9 cells exhibited a normal XX karyotype by standard G-banding techniques (20 chromosomal spreads analyzed). However, seven months after derivation, in a single karyotype preparation, 16/20 chromosomal spreads exhibited a normal XX karyotype, but 4/20 spreads demonstrated random abnormalities, including one with a translocation to chromosome 13 short arm, one with an inverted chromosome 20, one with a translocation to the number 4 short arm, and one with multiple fragmentation. Subsequently, at 8, 10, and 12.75 months after derivation, H9 cells exhibited normal karyotypes in all 20 chromosomal spreads examined.

We observed that the cloning efficiency of human ES cells in previously described culture conditions that included animal serum was poor (regardless of the presence or absence of bFGF). We also observed that in the absence of animal serum the cloning efficiency increased, and increased even more with bFGF.

The data expressed below is the total number of colonies resulting from $10^5$ individualized ES cells plated, +/–standard error of the mean (percent colony cloning efficiency). With 20% fetal serum and no bFGF there was a result of 240+/–28. With 20% serum and bFGF the result was about the same, 260+/–12. In the absence of the serum (presence of 20% serum replacer) the result with no bFGF was 633+/–43 and the result with bFGF was 826+/–61. Thus, serum adversely affected cloning efficiency, and the presence of the bFGF in the absence of serum had an added synergistic benefit insofar as cloning efficiency.

The long term culture of human ES cells in the presence of serum does not require the addition of exogenously supplied bFGF, and (as noted above) the addition of bFGF to serum-containing medium does not significantly increase human ES cell cloning efficiency. However, in serum-free medium, bFGF increased the initial cloning efficiency of human ES cells.

Further, I have discovered that supplying exogenous bFGF is very important for continued undifferentiated proliferation of primate embryonic stem cells in the absence of animal serum. In serum-free medium lacking exogenous bFGF, human ES cells uniformly differentiated by two weeks of culture. Addition of other factors such as LIF (in the absence of bFGF) did not prevent the differentiation.

The results perceived are particularly applicable to clonal lines. In this regard, clones for expansion were selected by placing cells individually into wells of a 96 well plate under direct microscopic observation. Of 192 H-9 cells plated into wells of 96 well plates, two clones were successfully expanded (H-9.1 and H-9.2). Both of these clones were subsequently cultured continuously in media supplemented with serum replacer and bFGF.

H9.1 and H9.2 cells both maintained a normal XX karyotype even after more than 8 months of continuous culture after cloning. The H-9.1 and H-9.2 clones maintained the potential to form derivatives of all three embryonic germ layers even after long term culture in serum-free medium. After 6 months of culture, H9.1 and H9.2 clones were confirmed to have normal karyotypes and were then injected into SCID-beige mice.

Both H9.1 and H9.2 cells formed teratomas that contained derivatives of all three embryonic germ layers including gut epithelium (endoderm) embryonic kidney, striated muscle, smooth muscle, bone, cartilage (mesoderm), and neural tissue (ectoderm). The range of differentiation observed within the teratomas of the high passage H9.1 and H9.2 cells was comparable to that observed in teratomas formed by low passage parental H9 cells.

It should be appreciated from the description above that while animal serum is supportive of growth it is a complex mixture that can contain compounds both beneficial and detrimental to human ES cell culture. Moreover, different serum batches vary widely in their ability to support vigorous undifferentiated proliferation of human ES cells. Replacing serum with a clearly defined component reduces the variability of results associated with this serum batch variation, and should allow more carefully defined differentiation studies.

Further, the lower cloning efficiency in medium containing serum suggests the presence of compounds in conventionally used serum that are detrimental to stem cell survival, particularly when the cells are dispersed to single cells. Avoiding the use of these compounds is therefore highly desired.

The present invention has been described above with respect to its preferred embodiments. Other forms of this concept are also intended to be within the scope of the claims. For example, while recombinantly produced human basic fibroblast growth factor was used in the above experiments, naturally isolated fibroblast growth factor should also be suitable. Further, these techniques should also prove suitable for use on monkey and other primate cell cultures.

Thus, the claims should be looked to in order to judge the full scope of the invention.

INDUSTRIAL APPLICABILITY

The present invention provides methods for culturing primate embryonic stem cells, and culture media for use therewith.

I claim:

1. A method of culturing primate embryonic stem cells in defined media without serum, the method comprising:
   culturing the primate embryonic stem cells in a culture medium containing albumin, amino acids, vitamins, minerals, at least one transferrin or transferrin substitute, and at least one insulin or insulin substitute, the culture medium being essentially free of mammalian fetal serum and containing exogenously supplied human fibroblast growth factor that is supplied from a source other than just a fibroblast feeder layer, so that the stem cells proliferate in culture and remain undifferentiated in the absence of serum in the medium.

2. The method of claim 1, wherein the culture is essentially free of any animal serum.

3. The method of claim 2, wherein the culture also comprises a fibroblast feeder layer.

4. The method of claim 2, wherein the fibroblast growth factor is basic fibroblast growth factor.

5. The method of claim 4, wherein the fibroblast growth factor is human basic fibroblast growth factor which has been produced from a recombinant gene.

6. The method of claim 5, wherein the human basic fibroblast growth factor is present in the culture in a concentration of at least 0.1 ng/ml for at least a portion of the method.

7. The method of claim 2, wherein the primate embryonic stem cells are human embryonic stem cells.

8. A method of culturing primate embryonic stem cells in defined media without serum, the method comprising:
   culturing the primate embryonic stem cells in a culture medium containing albumin, amino acids, vitamins minerals, at least one transferrin or transferrin substitute, and at least one in or insulin substitute, the culture medium being essentially free of mammalian fetal serum and containing exogenously supplied mammalian fibroblast growth factor that is supplied from a source other than just a fibroblast feeder layer, said culturing step being conducted for over one month with the embryonic stem cells proliferating in culture while maintaining the potential of the stem cells to differentiate into derivatives of endoderm, mesoderm, and ectoderm tissues, and while maintaining the karyotype of the stem cells.

9. A method of culturing primate embryonic stem cells in defined media without serum, the method comprising:
   culturing the stem cells in a culture medium containing albumin, amino acids, vitamins, minerals, at least one transferrin or transferrin substitute, and at least one insulin or insulin substitute, the culture medium being essentially free of mammalian fetal serum and in the presence of a fibroblast growth factor capable of activating a fibroblast growth factor signaling receptor, wherein the growth factor is exogenously supplied to the culture from a source other than just a fibroblast feeder layer, so that the stem cells proliferate in culture and remain undifferentiated in the absence of serum in the medium.

10. The method of claim 9, wherein the culture is essentially free of any animal serum.

11. The method of claim 10, wherein the culture also comprises a fibroblast feeder layer.

12. The method of claim 10, wherein the primate embryonic stem cells are human embryonic stem cells.

13. A method of culturing primate embryonic stem cells in defined media without serum, the method comprising:
   culturing the primate embryonic stem cells in a culture medium containing albumin, amino acids, vitamins, minerals, at least one transferrin or transferrin substitute, and at least one insulin or insulin substitute, the culture medium being essentially free of mammalian fetal serum and in the presence of a fibroblast growth factor capable of activating a fibroblast growth factor signaling receptor, wherein the growth factor is exogenously supplied to the culture from a source other than just a fibroblast feeder layer, said culturing step being conducted for over one month with the embryonic stem cells proliferating in culture while maintaining the potential of the stem cells to differentiate into derivatives of endoderm, mesoderm, and ectoderm tissues, and while maintaining the karyotype of the stem cells.

14. In a method of culturing primate embryonic stem cells without serum, the improvement comprising:
   culturing the primate embryonic stem cells in a culture free of added mammalian fetal serum but including albumin, vitamins, minerals, insulin, and transferrin, and in the presence of fibroblast growth factor that is exogenously supplied to the culture from a source other than just a fibroblast feeder layer, so that the stem cells proliferate in culture and remain undifferentiated in the absence of serum in the medium.

* * * * *